United States Patent [19]
Mitchell et al.

[11] 4,083,995
[45] Apr. 11, 1978

[54] (Z)-9-TETRADECEN-1-OL FORMATE AND ITS USE AS A COMMUNICATION DISRUPTANT FOR HELIOTHIS

[75] Inventors: Everett R. Mitchell, Gainesville, Fla.; Martin Jacobson, Silver Springs, Md.; Alfred H. Baumhover, Oxford, N.C.

[73] Assignee: The United States of America as represented by the Secretary of Agriculture, Washington, D.C.

[21] Appl. No.: 748,031

[22] Filed: Dec. 6, 1976

Related U.S. Application Data

[62] Division of Ser. No. 707,792, Jul. 22, 1976, abandoned.

[51] Int. Cl.$^2$ .............................................. A01N 9/24
[52] U.S. Cl. .................................................. 424/311
[58] Field of Search ........................... 424/84, 311, 314

[56] References Cited
PUBLICATIONS

Chemical Abstracts, vol. 83 (1975), pp. 159094u, 111385n.
Chemical Abstracts, Vol. 84 (1976), p. 16718k.

*Primary Examiner*—V. D. Turner
*Attorney, Agent, or Firm*—M. Howard Silverstein; David G. McConnell; Salvador J. Cangemi

[57] ABSTRACT

(Z)-9-Tetradecen-1-ol formate [(Z)-9-TDF], a chemical of nonbiological origin, was prepared and found to have excellent potential as an insect control agent for the corn earworm, *Heliothis zea* (Boddie) and tobacco budworm, *H. virescens* (F.). Mating of *H. zea* and *H. Virescens* moths exposed in the field to an atmosphere permeated with (Z)-9-TDF was greatly reduced. The chemical can be used alone to inhibit mating of *H. zea* or *H. virescens* or it can be dispensed together with other mating inhibitors to suppress mating in several pest species simultaneously.

1 Claim, No Drawings

(Z)-9-TETRADECEN-1-OL FORMATE AND ITS USE AS A COMMUNICATION DISRUPTANT FOR HELIOTHIS

This is a division of application Ser. No. 707,792, filed July 22, 1976, now abandoned.

FIELD OF THE INVENTION

This invention relates to a compound (Z)-9-tetradecen-1-ol formate (TDF) and the use thereof particularly as a specific inhibitor for controlling the mating behavior of the corn earworm, *Heliothis zea* (Boddie), and the tobacco budworm, *H. virescens* (F.), by functioning to disrupt pheromone communications.

DESCRIPTION OF THE PRIOR ART

Recent research has demonstrated that pheromonal communication between the sexes of several species of Lepidoptera can be effectively disrupted by permeating the air with synthetic compounds identical or similar to the true pheromones of the target species. The disruption technique has been used to suppress *Pectinophora gossypiella* (Saunders) larval populations in cotton, due ostensibly to the males' inability to locate females and mate (Shorey et al, Entomol. 67:347-50). This technique, therefore, has potential for inhibiting reproduction of the corn earworm and the tobacco budworm, two American insects that are serious pests in highly diverse eco-systems.

The sex pheromone of *H. virescens* consists of two compounds (Z)-11-hexadecenal (HDAL) and (Z)-9-tetradecenal (TDAL) (Roelofs et al, 1974, Life Sci. 14:1555-62; Tumlinson et al, 1975, J. Chem. Ecol. 1:203-14). Also, *H. zea* has (Z)-11-HDAL as a part of its system though there is no evidence that (Z)-9-TDAL is involved (Roelofs et al, 1974, Life Sci. 14:1555-62). Priesner et al (1975 Z, Naturforsch 30:283-93) reported electroantennogram data reflecting response of male pheromone receptors for 16 species of Noctuidae (Lepidoptera) including *H. zea*. In this species, (Z)-9-TDF (a structure unknown as an insect pheromone) was approximately 30 times more effective than the reported pheromone constituent, (Z)-11-HDAL.

We, therefore, evaluated the (Z) and (E) isomers of 9-tetradecen-1-ol formate and (E)-9-tetradecen-1-ol as mating inhibitors for *H. zea* and *H. virescens*.

SUMMARY OF THE INVENTION

The disruptive effect of the candidate compounds first was assessed by determining whether males could locate pheromone releasing females placed at the center of small field plots when the males were simultaneously exposed to an atmosphere permeated with the test compound. Thus, two-four experimental areas (including a control) separated by a minimum of 100 m were established in an abandoned tobacco field that was heavily infested with weeds and had corn on two sides. The 81-m² treatment plots were randomly aligned in a row perpendicular to the prevailing wind. The compounds were evaporated into the air from 16 dispensers arrayed at intervals of 3 m in a 4 × 4 checkerboard pattern. The dispensers were polyethylene caps (OS-6 natural polyethylene closures, Scientific Products) held ca. 1 m above the soil surface on wooden stakes. Each dispenser contained 25 mg of the test chemical. The cap dispensers released the compounds at a rate of ca. 300 ng/min at 27° C and 0.4 m/sec wind velocity. One or two cylindrical electric grid traps (Mitchell et al, 1972, Eviron. Entomol. 1:365-8) baited with three 2-day-old virgin females were positioned in the center of each plot. The *H. zea* and *H. virescens* females used as bait were reared in the laboratory from larval maintained on artificial diet. Bait females were replaced every 3 or 4 days. Captured insects were collected and counted daily, and the treatments were rotated one position.

Although the 9-TDF used in this experiment contained 86% of the (Z) isomer and 12% of the (E) isomer, (Z)-9-TDF reduced the capture of *H. zea* and H. virescens male moths in the female-baited traps by 95% (Table 1). None of the other materials had any significant effect. The relatively large quantity of the (E) isomer in the mixture did not appear to alter effectiveness against either *H. zea* or *H. virescens*. This was later confirmed by comparing the capture of male moths in plots treated with 100% (Z)-9-TDF or 86% pure (Z)-9-TDF. Again captures of male H. zea were reduced >95%.

TABLE I

Efficacy of individual compounds in disrupting pheromonal communication based on captures of male *H. virescens* and *H. zea* in 9-baited traps.

| Chemical | X no. ♂ captured/trap/night* Control | Treatment |
|---|---|---|
| *H. zea* | | |
| (E)-9-TDF | 96.7 a | 96.9 a |
| (E)-9-TDOL | 96.7 a | 101.3 a |
| (E)-9-TDP | 136.9 a | 5.1 b |
| *H. virescens* | | |
| (E)-9-TDF | 5.8 a | 5.7 a |
| (E)-9-TDOL | 5.8 a | 4.2 a |
| (E)-9-TDF | 20.7 a | 1.7 b |

*Means in the same row followed by the same letter are homogenous ($P = 0.05$, Student's t-test). t The relationship between reductions in trap capture and mating by virgin females of *H. zea* and *H. virescens* in field plots treated with (Z)-9-TDF was determined as follows.

A treated plot and a control were set up ca. 60 m apart, perpendicular to the prevailing wind. (Z)-9-TDF was evaporated into the air from polyethylene vials (36 ea containing 25 mg chemical) arrayed at intervals of ca. 3 m in a 6 × 6 checkerboard pattern (ca. 0.02 ha). Each vial, which released the chemical at about 300 ng/min, was held ca. 1 m above the soil surface on a wooden stake. The treatment and control were rotated daily (= replicate). The disruptive effect of (Z)-9-TDF was assessed by determining whether laboratory-reared females placed on plants located near the center of test plots of cotton or corn would mate with feral males. Plants in this control area were encircled with an aluminum ring (1.1 m diam., 15.2 cm high). The inner surface of the ring was dusted with talc to discourage the moths from climbing up the surface of the band and excaping. A circular screen cage of hardware cloth, 1.2 m high and slightly larger in diameter than the ring, was positioned over the release site to protect the test insects from birds. The openings (mesh) in the top and side of the screen cage were ca. 40 mm high and 80 mm long.

The wings of laboratory-reared females (10-15/plot) were clipped, and then they were released onto the plants just before sundown. The females were collected the following morning and dissected. The presence of a spermatophore in the bursa copulatrix indicated mating. Because several of the females released on any given night either escaped or were eaten by insect predators, the percent reduction in mating necessarily was based upon the number of females actually recaptured: thus percent reduction in mating =
$$\frac{\text{percent ♀ mated controls} - \text{percent ♀ mated treated}}{\text{percent ♀ mated controls}} \times 100.$$

The effect of (Z)-9-TDF on moth captures in electric grid traps baited with three *H. zea* females or three *H. virescens* females was evaluated in plots of the same size and design (6 × 6 checkerboard) as those used in the mating experiments.

There was a very close correlation between the reduction in capture of males by female-baited traps and the reductions in mating by females of *H. zea* and *H. virescens* in small fields plots treated with (Z)-9-TDF (Table II).

TABLE II

Efficacy of (Z)-9-tetradecen-1-ol formate in disrupting pheromonal communication (relative to controls) in *H. zea* and *H. virescens* based on captures of ♂ in ♀-baited traps and mating by ♀ placed on plants.

| Species | Reduction in trap captures (%)* | Reduction in mating (%)* |
| --- | --- | --- |
| H. zea | 98.6 (10) | 96.7 (14) |
| H. virescens | 86.6 (16) | 81.2 (12) |

*Moth captures and matings were reduced significantly by the treatment ($P = 0.05$, Student's t-test).

(Z)-9-TDF and (Z,E)-9,12-tetradecadien-1-ol acetate (TDDA) were evaporated simultaneously in the same plot to determine whether we could achieve concurrent disruption of mating of *H. zea* and the fall armyworm, *Spodoptera frugiperda* (J. E. Smith). Preliminary experiments had established that (Z)-9-TDF did not affect mating in *S. frugiperda*; likewise, (Z,E)-9,12-TDDA had no effect on *H. zea* mating. Two vials (each containing 25 mg chemical) were attached to wooden stakes and arranged in a corn field in a 5 × 5 checkerboard pattern as described. Separate mating rings were established near the center of the treated plot. The treatment and control were rotated daily (total 8 replicates).

This experiment was repeated using microencapsulated formulations of (Z)-9-TDF and (Z,E)-9,12-TDDA. The formulations were mixed immediately prior to application to plots of field corn. Then the chemicals were applied at the rate of ca. 3.5 g (Z)-9-TDF in one liter formulation plus an equal quantity of (Z,E)-9,12-TDDA to 484 m² plots with a ULV backpack sprayer. The materials were applied to three different plots (replicates) at 10–14 day intervals.

The data shown in Table III demonstrates the feasibility of simultaneously dispensing (Z)-9-TDF and other disruptants, such as (Z,E)-9-TDA, to achieve concurrent disruption of mating in two or more pest species. In the plots where microencapsulated formulations of (Z)-9-TDF and (Z,E)-9,12-TDDA were applied, disruption of mating in both *H. zea* and *H. virescens* was >90% for 5 days or more, depending upon the amount and duration of rainfall.

TABLE III

Efficacy of compounds in disrupting mating (relative to controls) in *H. zea* and *S. frugiperda* when materials were evaporated simultaneously in the same plot.

| Chemical | % reduction in mating* | |
| --- | --- | --- |
|  | H. zea | S. frugiperda |
| (Z)-9-TDF | 96.7 | |
| (Z,E)-9,12-TDDA |  | 88.3 |
| (Z,E)-9,12-TDDA + (Z)-9-TDF | 87.6 | 92.7 |

*Matings in all treatments reduced significantly ($P = 0.05$, Student's t-test).

DESCRIPTION OF THE PREFERRED EMBODIMENTS

A route is disclosed for the synthesis of (Z)-9-tetradecen-1-ol formate (I), which is the formic acid ester of (Z)-9-tetradecen-1-ol and has the following formula:

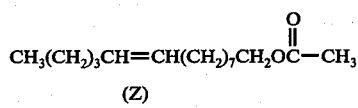

(Z)

It is a clear, oily-feeling, slightly viscous colorless liquid with a mild odor. It is insoluble in water but readily soluble in hexane, ethyl ether, acetone, benzene, and other organic solvents. On the basis of its structure, it probably has a very low toxicity to mammals, birds, fish, and insects.

Since the structure of I is relatively simple, the compound can be prepared by a number of synthetic routes. For the purposes of this invention procedures employed by Warthen [J. Med. Chem., 11, 371 (1968)] were used to prepare tetrahydro-2-(9-tetradecynyloxy)pyran (V), from which (Z)-9-tetradecen-1ol (VI) and I were then prepared.

The hydroxyl group of 8-chloro-1-octanol (II) is protected by treatment with dihydropyran under acid conditions to form 2[8-chlorooctyl)oxy]tetrahydropyran (III). Compound (III) dissolved in dimethyl sulfoxide is caused to react at low temperature with lithium acetylide-ethylene diamine complex to yield 2-(9-decynyloxy)tetrahydropyran (IV), whose lithium salt (prepared with lithium amide in dioxane) is condensed with n-butyl bromide to yield compound (V).

Compound (V) is converted in one step to (Z)-9-tetradecen-1-ol (VI) by hydrogenating in methanol with 5% palladium on calcium carbonate (using a little quinoline to stop the hydrogenation at the double-bond stage), then adding sulfuric acid and stirring overnight.

Refluxing compound VI with 97% formic acid in dry benzene, continuously removing the water formed by means of a Dean-Stark trap, gives compound (I) in 78% yield. The product contains a minimum of 86% of the (Z) ester and can be used as such or may be easily purified by liquid chromatography.

EXAMPLE 1

2[(8-Chlorooctyl)oxy]tetrahydropyran (III)

Dihydropyran (22 g) was slowly dripped into a stirred mixture of 34 g of 8-chloro-1-octanol and 0.3 ml of concentrated HCl, which was cooled to keep the temperature below 40°. After the mixture was stirred for 3 hours at 25°, excess NaHCO₃ was added and the mixture was stirred for 1 hour, filtered, and distilled to give 48.0 g (92%) of II, B.P. 95°–98° (0.04 mm.), $N_D^{25}$ 1.4608.

EXAMPLE II

2-(9-Decynyloxy)tetrahydropyran (IV)

A solution of 11 g (0.044 mole) of compound III in 25 ml of dimethylsulfoxide (DMSO) was slowly added to a stirred slurry of 5.0 g of lithium acetylide-ethylene diamine complex in 25 ml of dry DMSO cooled to 10°–15°. The mixture was allowed to come to room temperature and was then stirred overnight. It was then diluted with 100 ml of ice and water, the layer were separated, and the aqueous phase was extracted four time with ether. The combined organic phase was washed twice with saturated NaCl solution and distilled to give 9.4 g (89%) of compound IV, B.P. 85°–88° (0.04 mm), $N_D^{25}$ 1.4590.

EXAMPLE III

Tetrahydro-2-(9-tetradecynyloxy)pyran (V)

A mixture of 7.4 g of compound IV, 1.0 g lithium amide, and 50 ml of dry, purified dioxane was stirred and refluxed 3.5 hours under nitrogen, cooled, 4.5 g of n-butyl bromide was added dropwise and the refluxing and stirring continued for 20 hours more. The mixture was chilled in an icebath, diluted with 60 ml of water and the layers separated. The aqueous layer was extracted three times with ether, the combined organic phase was washed three times with saturated NaCl solution, the solvents were evaporated and the residue distilled to give 3.2 g (36%) of compound V which boiled at 120°–123° (0.03 mm), $N_D^{25}$ 1.4634.

EXAMPLE IV

(Z)-9-Tetradecen-1-ol (V)

Compound V (3.0 g, 0.01 mole) was dissolved in 25 ml of absolute methanol, and 0.12 g of 5% palladium on CaCO$_3$ was added along with one drop of quinoline to "poison" the catalyst. The compound was hydrogenated at 27° until one mole of hydrogen had been absorbed and reaction came to a stop. The solution was filtered, diluted with an additional 50 ml of methanol, 20 ml of 25% H$_2$SO$_4$ was added, and the mixture was stirred at room temperature for 24 hours. The solution was diluted with 75 ml of H$_2$O, extracted three times with ether, and the combined extracts were washed with several portions of 10% NaHCO$_3$ followed by saturated NaCl solution. Evaporation of the solvents and distillation of the residue gave 1.9 g (90%) of compound VI as a colorless liquid boiling at 115° (0.2 mm), $N_D^{25}$ 1.4561.

EXAMPLE 5

(Z)-9-Tetradecen-1-ol formate (I)

A mixture of 11 g of compound VI and 11 g of 97% formic acid in 50 ml of dry benzene was relfuxed for 6 hours, continuously removing the water formed with a Dean-Stark trap. The cooled solution was treated with 100 ml each of H$_2$O and ether, and the organic layer was washed several times with cold H$_2$O, 10% NaHCO$_3$ solution, and saturated with NaCl solution, then dried with Na$_2$SO$_4$. Evaporation of solvent and distillation gave 9.7 g (78%) of compound I as a colorless liquid boiling at 103°–108° (0.2 mm), $N_D^{25}$ 1.4464.

Gas chromatographic analysis: A capillary column (300 ft. ×0.02 in.) coated with diethylene glycol succinate was used. The carrier gas was helium, flow rate 4.2 ml/min., and the column temperature 150°. A minor peak (E) and a major peak (Z) were obtained with elution times of 22.5 and 23.5 minutes, respectively. The composition calculated for 86% (Z) and 12% (E).

Infrared spectrum: There were absorption peaks at 2850–2940 (C-H) and 1175 cm$^{-1}$ (primary formate). A small peak at 970 cm.$^{-1}$ indicated the presence of a few percent of the (E) isomer of I.

Analysis - Calcd. for $C_{15}H_{28}O_2$ (percent): C, 75.00; H, 11.67. Found (percent): C, 74.91; H, 11.69.

Although the product thus prepared could be used without further treatment for the purposes described in this patent application, it could be separated into pure (Z) and (E) isomers by liquid column chromatography on a 1.1 cm (ID) column packed to a height of 36 cm with a hexane slurry of 100/140 mesh silver nitrate (25%)-treated silica gel. The column was loaded with 0.5 ml of I and eluted successively with 200 ml of hexane-ether (97:3) and 200 ml of hexane-ether (94.6). The (97.3) fraction was enriched with the (E) formate and the (94.6) fraction contained 100% (Z) formate.

We claim:

1. A method of controlling mating in the corn earworm, *Heliothis zea* and the tobacco budworm, *H. virescens* which comprises contacting them with a mating inhibiting amount of (Z)-9-tetradecen-1-ol formate.

* * * * *